(12) United States Patent
Dehaven

(10) Patent No.: US 10,088,393 B2
(45) Date of Patent: Oct. 2, 2018

(54) WATER SAMPLING DEVICE

(71) Applicant: Russ Dehaven, Gering, NE (US)

(72) Inventor: Russ Dehaven, Gering, NE (US)

( * ) Notice: Subject to any disclaimer, the term of this patent is extended or adjusted under 35 U.S.C. 154(b) by 287 days.

(21) Appl. No.: 14/708,901

(22) Filed: May 11, 2015

(65) Prior Publication Data
US 2015/0330874 A1 Nov. 19, 2015

Related U.S. Application Data

(60) Provisional application No. 61/994,283, filed on May 16, 2014.

(51) Int. Cl.
G01N 1/20 (2006.01)
B01L 1/00 (2006.01)

(52) U.S. Cl.
CPC .............. *G01N 1/2035* (2013.01); *B01L 1/00* (2013.01); *B01L 2200/141* (2013.01); *G01N 2001/205* (2013.01); *G01N 2001/2071* (2013.01)

(58) Field of Classification Search
CPC ............................................. G01N 2001/2071
See application file for complete search history.

(56) References Cited

U.S. PATENT DOCUMENTS

| 4,683,761 A * | 8/1987 | Stock ................. G01N 1/14 73/864.34 |
| 4,989,463 A * | 2/1991 | Cimaglia ................. B01L 1/00 141/97 |
| 5,730,765 A * | 3/1998 | Henry ................. B01L 1/02 454/184 |
| 5,918,290 A * | 6/1999 | Auck ................. G01M 1/00 73/863.81 |
| 6,428,122 B1 | 8/2002 | Henry et al. |
| 2006/0119232 A1* | 6/2006 | Tattershall ................. B01L 1/50 312/1 |
| 2007/0122870 A1 | 5/2007 | Turley et al. |
| 2007/0217960 A1* | 9/2007 | Sekela ................. B01L 1/02 422/400 |
| 2008/0056936 A1 | 3/2008 | Lack |
| 2009/0223664 A1* | 9/2009 | Hayworth ............. E21B 21/062 166/264 |

* cited by examiner

*Primary Examiner* — Robert R Raevis
(74) *Attorney, Agent, or Firm* — Santangelo Law Offices, PC

(57) ABSTRACT

A water sampling device for obtaining a water sample within an environment isolated from adverse weather conditions, such as rain or a debris filled atmosphere. The water sampling device includes a chamber having a base, one or more sidewalls, and an upper end. The interior of the chamber includes a faucet disposed on a sidewall and connected to a hose that extends through the sidewall to the exterior of the chamber, wherein the hose can collect water from a water source. A valve is disposed within the faucet in order to control the flow of water therethrough. The water sampling device further includes a pair of gloves disposed on opposing sidewalls, wherein the gloves extend into the chamber so as to allow a user to manipulate the water sample therein. A stand is secured to the exterior of the chamber in order to support the chamber in an upright position.

24 Claims, 4 Drawing Sheets

WATER SAMPLING DEVICE

CROSS REFERENCE TO RELATED APPLICATION

This application claims the benefit of U.S. Provisional Application No. 61/994,283 filed on May 16, 2014. The above identified patent application is herein incorporated by reference in its entirety to provide continuity of disclosure.

BACKGROUND OF THE INVENTION

Field of the Invention

The present invention relates to water sampling devices. More specifically, the present invention provides a water sampling device comprising a chamber having a pair of gloves extending therein. The interior of the chamber further comprises a faucet connected to an external hose, wherein the hose transfers the water sample to the faucet so a user can access the sample within the chamber via the pair of gloves. The upper end of the chamber comprises an opening removably sealed by a cover so as to allow the sample to be removed from the chamber.

Many municipalities and other local administrations require the frequent testing of water from various sources, such as water transmission mains. Testing of a water source is also required prior to installing a new water line. Samples are obtained from these sources and are then transported to a laboratory for testing in order to determine if harmful bacteria, such as coliform or *escherichia coli*, has contaminated the source.

When obtaining a sample for testing, environmental factors, such as unfavorable weather conditions, are detrimental to acquiring accurate test results. A rainy or muddy environment lead to dilution or contamination of the water sample. Therefore, an individual obtaining a water sample is required to wait for suitable weather conditions prior to obtaining a sample. The delay causes frustration to the individual obtaining the water sample, as well as to the individuals responsible for installation of a new water line. The delay in testing can result in an entire construction project becoming delayed. Furthermore, public health can be at risk in the interim. Some individuals choose to perform a test regardless of the adverse weather conditions, which may result in inaccuracies that can affect the public health. Therefore, there exists a need in the prior art for a device that allows an individual to obtain a proper water sample in adverse weather conditions.

It is submitted that the present invention substantially diverges in design elements from the prior art and consequently it is clear that there is a need in the art for an improvement to existing water sampling devices. In this regard the instant invention substantially fulfills these needs.

SUMMARY OF THE INVENTION

In view of the foregoing disadvantages inherent in the known types of water sampling devices now present in the prior art, the present invention provides a new water sampling device wherein the same can be utilized for providing convenience for the user when obtaining and testing a sample of water in adverse weather conditions.

It is therefore an object of the present invention to provide a new and improved water sampling device that has all of the advantages of the prior art and none of the disadvantages.

It is another object of the present invention to provide a water sampling device comprising a chamber having a base, one or more sidewalls, and an upper end, wherein the chamber is adapted to isolate a water sample therein from adverse weather conditions.

Another object of the present invention is to provide a water sampling device comprising a pair of gloves extending into the chamber, wherein each glove is disposed on opposing sidewalls thereof in order to manipulate a water sample therebetween.

Yet another object of the present invention is to provide a water sampling device wherein the interior of the chamber comprises a faucet disposed on a sidewall and connected to an external hose, wherein the hose is adapted to transfer a water to the faucet for sampling.

Yet another object of the present invention is to provide a water sampling device wherein the upper end and base of the chamber each comprise an opening so as to allow a water sample to be removed therefrom and allow liquid to pass therethrough in order to sanitize the interior of the chamber.

Yet another object of the present invention is to provide a water sampling device further comprising one or more holsters disposed on an interior sidewall of the chamber adapted to support water sampling equipment thereon.

Yet another object of the present invention is to provide a water sampling device further comprising one or more windows disposed on a sidewall of the chamber so as to allow a user to view the interior of the chamber.

Another object of the present invention is to provide a water sampling device that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
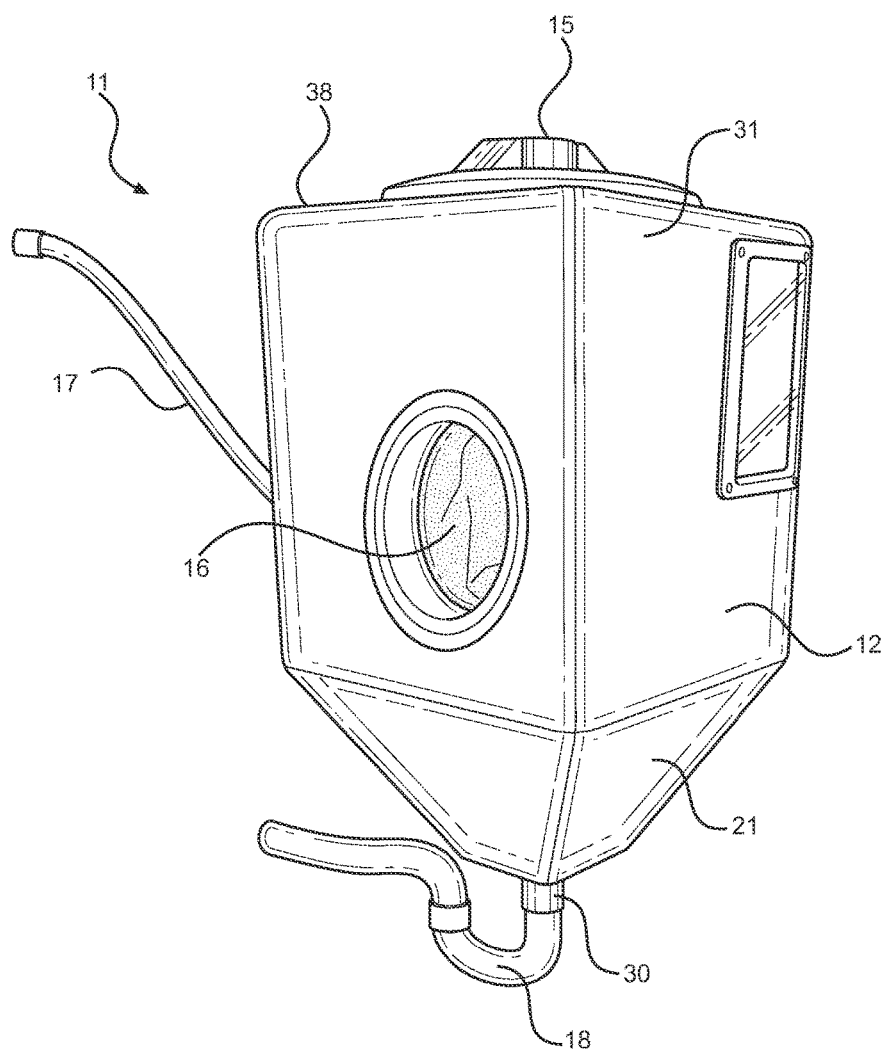
FIG. 1 shows a front perspective view of an embodiment of the water sampling device.

Reference is made herein to the attached drawings. Like reference numerals are used throughout the drawings to depict like or similar elements of the water sampling device. For the purposes of presenting a brief and clear description of the present invention, the preferred embodiment will be discussed as used for obtaining and testing water samples in poor weather conditions. The figures are intended for representative purposes only and should not be considered to be limiting in any respect.

Figure 2:
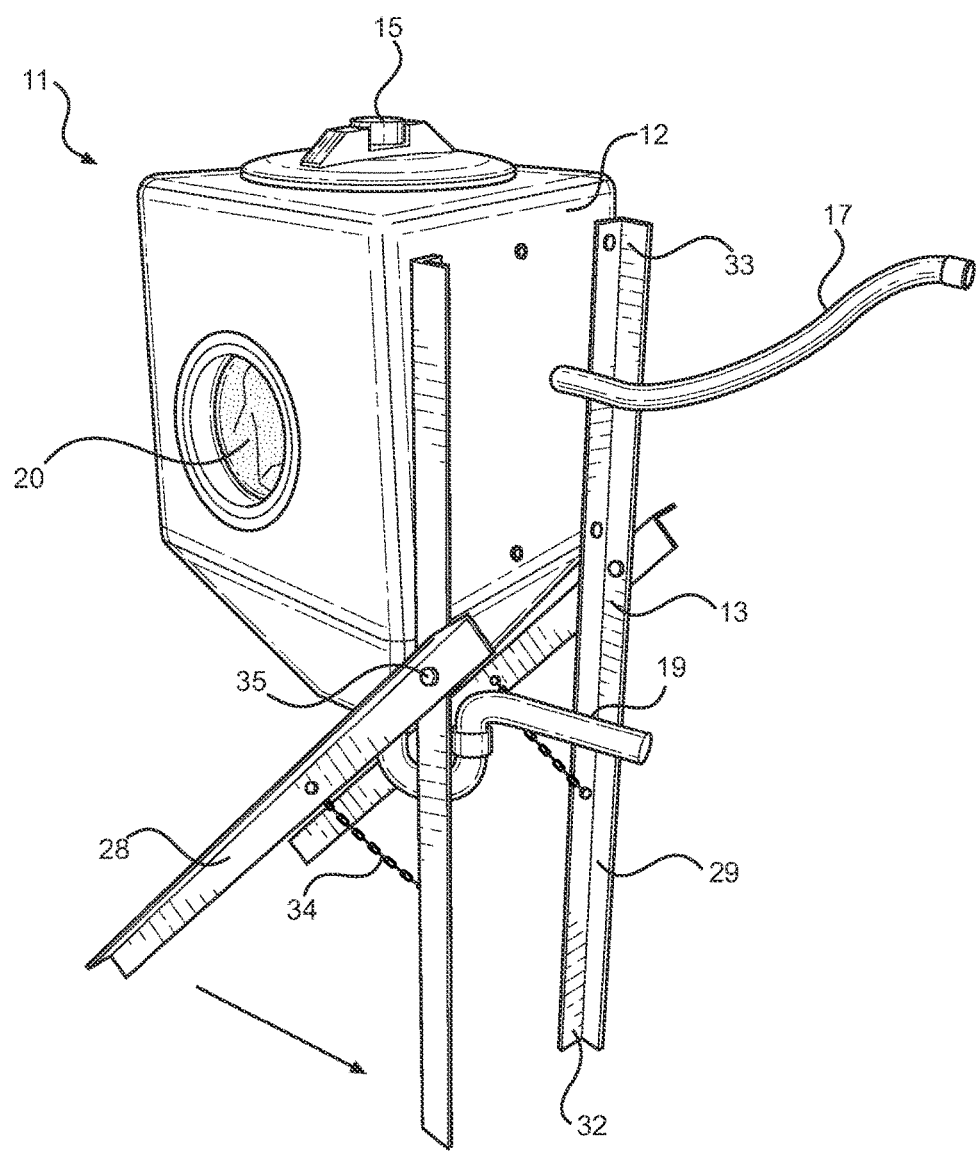
FIG. 2 shows a rear perspective view of an embodiment of the water sampling device.

Referring now to FIGS. 1 and 2, there is shown a front perspective view and a rear perspective view of the water sampling device. The water sampling device 11 is adapted to allow a user to collect one or more water samples in adverse weather conditions, such as a rainy or muddy environment, in order to test for the presence of harmful bacteria. The water sampling device 11 comprises a chamber 12 having one or more sidewalls 31, an upper end 38, and a base 21, wherein the chamber 12 is composed of any suitable material, such as high density polyethylene. The upper end 38 of the chamber 12 includes an upper opening that allows access to the interior thereof in order to remove a water sample from the chamber 12. In this way, water that enters the water sampling device 11 can be collected via a sample bottle, or the like, disposed within the chamber 12 and then removed therefrom for testing. The upper opening is removably sealed by a cover 15 so as to prevent debris and other elements, such as rain, from entering the chamber 12. The top of the cover 15 comprises a handle disposed on the center thereof so as to allow the cover 15 to be lifted from the upper opening. The diameter of the cover 15 is preferably the same diameter as the upper opening so as to fit within the upper opening and create a seal. The upper opening and cover 15 are circular in shape. However, in other embodiments, the upper opening and cover 15 can be any suitable shape, such as a square, as long as the cover 15 removably seals the upper opening.

The chamber 12 is primarily rectangular in shape with the exception of a tapered base 21. The base 21 is tapered from the lower edge of each sidewall 31 towards the lower end of the chamber 12. The base 21 further includes a drain opening 30 disposed at the lower end of the chamber 12, wherein the tapering of the base 12 provides a slope so as to allow fluids to easily travel to the lower end of the chamber 12 and vacate therefrom. In this way, the chamber 12 is adapted to be sanitized, after a water sample has been collected, by flushing fluid through the upper opening and out through the drain opening 30. The water sampling device 11 further includes one or more pipes 19 secured to the drain opening 30 adapted to direct the vacated fluid away from the chamber 12 for disposal. The pipe 19 comprises a plumbing trap, such as a P-shaped trap 18, disposed thereon so as to prevent gases from entering the chamber 12 and contaminating a water sample therein. The dimension of the drain opening 30 is preferably the same as the dimension of the pipe 19 so as to prevent any gaps therebetween. The pipe 19 is attached to the drain opening 30 by any suitable fastener, such as threading disposed on the interface of the pipe 19 and drain opening 30.

The water sampling device 11 further comprises a stand 13 secured to the exterior of the chamber 12. The stand 13 includes a first pair of parallel supports 29 adjustably secured to a second pair of parallel supports 28, wherein the mass of the chamber 12 is uniformly distributed amongst the supports 28, 29 so as to hold the chamber 12 in an upright position. The second pair of supports 28 are adjustably secured to the first pair of supports by any suitable fastener 35, such as a nut and bolt. The fastener 35 is loosely secured so as to allow the position of the supports 28, 29 to be adjusted. The first pair of supports 29 are vertically positioned and secured to the exterior of the chamber 12, wherein the second pair of supports 28 are angled beneath the chamber 12. Each support 28, 29 comprises an L-shaped cross section having a first part 32 extending perpendicularly from a second part 33. The first part 32 of the first pair of supports 29 is secured to the exterior of the chamber 12 and rests flush thereagainst, wherein the second part 33 is adjustably secured to the second part 33 of the second pair of supports 28. The L-shaped cross section provides multiple points of attachment for each support 28 and stability to the stand 13. In other embodiments, the supports 28, 29 can comprise any suitable cross section, such as a T-shape, as long as the chamber 12 is supported in an upright position.

The stand 13 further comprises a locking mechanism that allows the second pair of supports 28 to maintain a desired angled position relative to the first pair of supports 29. In the illustrated embodiment, the locking mechanism comprises a first of chain 34 connecting one side of the stand and a second chain 34 connecting the opposing side of the stand 13, wherein the each chain 34 is fastened to the first parts 32 of the supports 28, 29. The stand 13 is adapted to fold, such that the second pair of supports 28 are aligned parallel to the first pair of supports 29 for a compact configuration.

Figure 3:
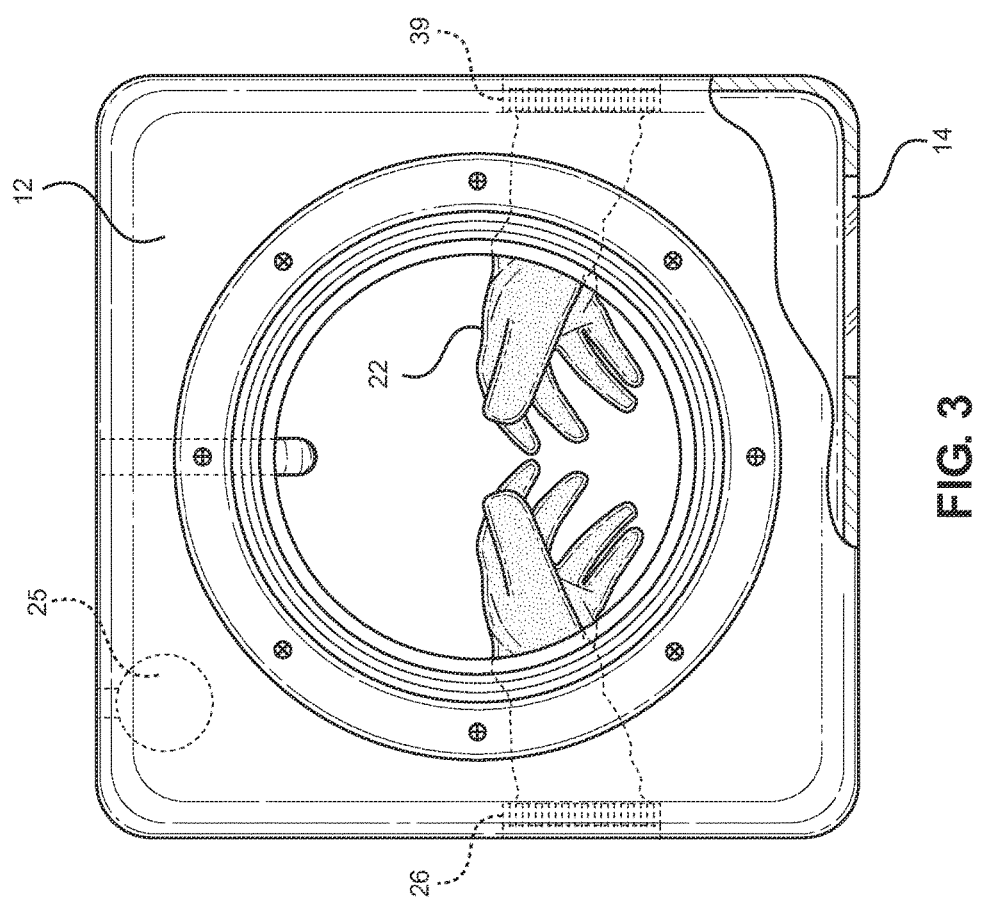
FIG. 3 shows a top down view of an embodiment of the interior of the water sampling device.

The water sampling device 11 further comprises a first aperture 16 disposed on a sidewall 31 and a second aperture 20 disposed on an opposing sidewall 31, wherein the apertures 16, 20 are adapted to receive a user's arms therethrough. The apertures 16, 20 are circular in shape. However, in other embodiments, the apertures 16, 20 can be any suitable shape, such as a square. Now referring to FIG. 3, there is shown a top down view of an embodiment of the interior of the water sampling device. Each aperture comprises a lip 39 perpendicularly extended into the interior of the chamber 12. The lip 39 extends around the perimeter of the aperture. The interior of the chamber 12 further comprises a pair of gloves 22 extending therein. The opening of each glove is secured around the lip 39 by any suitable fastener, such as compression clamp 26. The gloves 22 are composed of a chemical resistant material, such as butyl rubber. The gloves 22 are adapted to allow a user to manipulate a water sample within the chamber 12 so as not to contaminate the sample or the interior of the chamber 12.

The chamber 12 further comprises one or more windows 14 disposed on one or more sidewalls 31. The windows 14 allow a user to view the interior of the chamber 12 in order to manipulate a water sample therein. The window 14 is composed of any suitable transparent material, such as Plexiglas. The window 14 is rectangular in shape. However, in other embodiments, the window can be any suitable shape, such as a square or a circle.

The interior of the chamber 12 further comprises one or more holsters 25 adapted to hold sampling equipment therein, such as bottles. The holster 25 is attached to a sidewall by any suitable fastener, such as a screw. The holster 25 can be any suitable configuration as long as there is a horizontal surface area to support an object thereon. In the illustrated embodiment, the holster 25 is cylindrical in shape having a recessed area therein and an open upper end.

Figure 4:
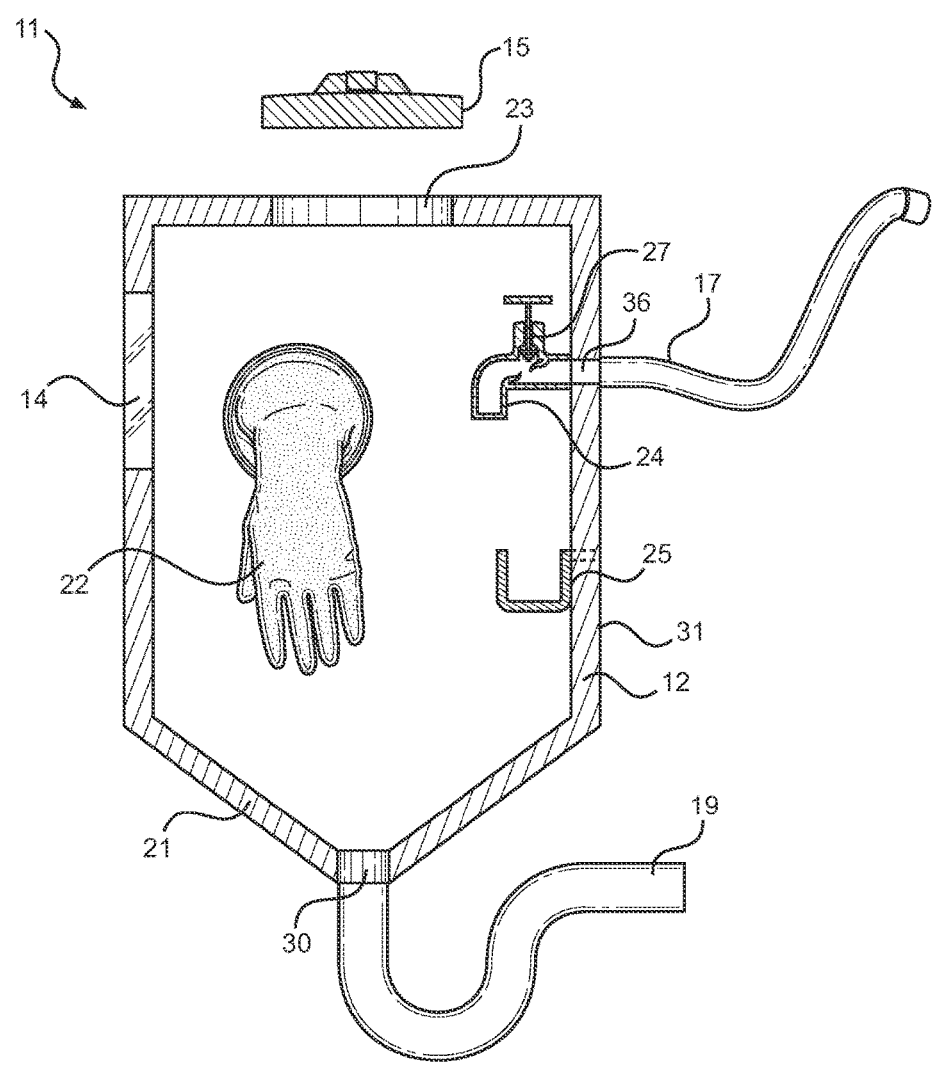
FIG. 4 shows a cross sectional view of an embodiment of the water sampling device.

Referring now to FIG. 4, there is shown a cross sectional view of an embodiment of the water sampling device. The water sampling device 11 further comprises a faucet 24 disposed on a sidewall 31 within the interior of the chamber 12. The faucet 24 permits liquid to flow into the chamber 12. The sidewall 31 in which the faucet 24 is disposed on is preferably positioned between the sidewalls 31 having the gloves 22 extending therefrom so as to allow a user to face towards the faucet 24 for convenient access thereto. The liquid receiving end of the faucet 24 is secured to an end of the hose 17 that extends through a channel 36 in the sidewall 31. The end of the hose 17 is secured to the channel 36 by any suitable fastener, such as a threaded interface. The opposing end of the hose 17 is disposed on the exterior of the chamber 12 adapted to collect and transfer water from an external source to the faucet 24. Water is delivered through the hose 17 by an external water source, such as a hydrant or service line.

The water sampling device 11 comprises a valve 27 within the faucet 24 in order to control the flow of water therethrough. Any suitable valve 27 can be used, such as a stop valve. In operation, the end of the hose 17 is connected to an external water source, wherein the fluid is delivered to the faucet 24 by any suitable means, such as a pump. A user places his or her arms through the gloves 22 and opens the valve 27 by turning the handle, wherein the stem of the valve 27 is lifted upwards. Once the valve is opened, fluid freely flows through the faucet 24 into the chamber 12. The user places a bottle or other container under the faucet 24 in order to collect a water sample therein. The user is able to view the interior of the chamber 12 through the window 14 disposed on the sidewall 31 that is opposing the sidewall 31 comprising the faucet 24 thereon. The sample is collected and the valve 27 is then closed. The bottle containing the water sample therein is placed on the holster 25. The user then removes his or her arms from the gloves 22 and removes the cover 15 from the upper opening 23, wherein the bottle is then removed from the chamber 12 and brought to a laboratory for testing. The chamber 12 is then flushed with fluid in order to sanitize the device 11, wherein the fluid is vacated through the drain opening 30 and disposed of through the pipe 19.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A water sampling device, comprising:
    a chamber comprising a base, four sidewalls, and an upper end, defining an interior chamber volume;
    a faucet disposed on a first sidewall of said four sidewalls and in said interior chamber volume, said faucet comprising a valve adapted to control liquid flow;
    a hose comprising a first end and a second end, wherein said second end extends from an exterior of said chamber and said first end is connected to said faucet;
    a pair of gloves secured to said chamber and extending therein, wherein a first glove is disposed on a second sidewall of said four sidewalls, said second sidewall being left of said first sidewall, and wherein a second glove is disposed on a third sidewall of said four sidewalls, said third sidewall being right of said first sidewall, and opposite said second sidewall;
    wherein said upper end of said chamber comprises an upper opening so as to allow access to said interior chamber volume, said upper opening removably sealed by a cover; one or more windows disposed on a fourth sidewall of said four sidewalls, said fourth sidewall opposite said first sidewall, said one or more windows adapted to allow a user to view said interior chamber volume;
    a drain opening disposed on said base of said chamber adapted to drain fluid therefrom; and
    at least one pipe secured to said drain opening adapted to direct fluid away from said chamber for disposal,
    wherein said at least one pipe comprises a P-shaped trap adapted to prevent gases from entering said chamber.

2. The water sampling device of claim 1, wherein said chamber is composed of high density polyethylene.

3. The water sampling device of claim 1, wherein said base of said chamber is tapered from a lower edge of said four sidewalls to a lower end of said chamber.

4. The water sampling device of claim 1, further comprising one or more holsters secured to said interior chamber volume.

5. The water sampling device of claim 1, wherein said chamber comprises a pair of apertures adapted to receive a user's arms therethrough; wherein each of said pair of apertures comprises a lip extending perpendicularly therefrom, such that said first glove is positioned over said lip of a first aperture and said second glove is positioned over said lip of a second aperture, wherein each of said first glove and said second glove is secured to a respective said lip by one or more glove fasteners.

6. The water sampling device of claim 5, wherein said one or more glove fasteners is a compression clamp.

7. The water sampling device of claim 1, wherein said first glove and said second glove are composed of butyl rubber.

8. The water sampling device of claim 1, further comprising a stand secured to said four sidewalls of an exterior of said chamber adapted to support said chamber in an upright position.

9. The water sampling device of claim 8, wherein said stand comprises a first pair of parallel supports and a second pair of parallel supports, wherein said first pair of parallel supports are adjustably secured to said second pair of parallel supports by fasteners, such that said first pair of parallel supports are adapted to align with said second pair of parallel supports in a compact configuration.

10. The water sampling device of claim 9, wherein a cross section of each of said first pair of supports and said second pair of supports is L-shaped.

11. The water sampling device of claim 9, further comprising a locking mechanism, wherein said locking mechanism includes a first chain connecting a support from said first pair of supports to a support from said second pair of supports, and a second chain connecting a parallel support from said first pair of supports to a parallel support from said second pair of supports, such that said first pair of supports are secured at a desired angle relative to said second pair of supports.

12. A water sampling device, comprising:
    a chamber comprising a base, four sidewalls, and an upper end, defining an interior chamber volume;
    a faucet disposed on a first sidewall of said four sidewalls and inside said chamber, said faucet comprising a valve adapted to control liquid flow;
    a hose comprising a first end and a second end, wherein said second end extends from an exterior of said chamber and said first end is connected to said faucet;
    a pair of gloves secured to said chamber and extending therein, wherein a first glove is disposed on a second sidewall of said four sidewalls, said second sidewall being left of said first sidewall, and wherein a second glove is disposed on a third sidewall of said four sidewalls, said third sidewall being right of said first sidewall and opposite said second sidewall;

wherein said upper end of said chamber comprises an upper opening so as to allow access to said interior chamber volume, said upper opening removably sealed by a cover;

one or more windows disposed on a fourth sidewall of said four sidewalls, said fourth sidewall opposite said first sidewall, said one or more windows adapted to allow a user to view said interior chamber volume; and one or more holsters secured to said interior chamber volume.

13. The water sampling device of claim 12, further comprising a drain opening disposed on said base of said chamber adapted to drain fluid therefrom.

14. The water sampling device of claim 13, further comprising at least one pipe secured to said drain opening adapted to direct fluid away from said chamber for disposal.

15. The water sampling device of claim 14, wherein said at least one pipe comprises a P-shaped trap adapted to prevent gases from entering said chamber.

16. The water sampling device of claim 12, wherein said chamber is composed of high density polyethylene.

17. The water sampling device of claim 12, wherein said base of said chamber is tapered from a lower edge of said four sidewalls to a lower end of said chamber.

18. The water sampling device of claim 12, wherein said chamber comprises a pair of apertures adapted to receive a user's arms therethrough; wherein each of said pair of apertures comprises a lip extending perpendicularly therefrom, such that said first glove is positioned over said lip of a first aperture and said second glove is positioned over said lip of a second aperture, wherein each of said first glove and said second glove is secured to a respective said lip by one or more glove fasteners.

19. The water sampling device of claim 18, wherein said one or more glove fasteners is a compression clamp.

20. The water sampling device of claim 12, wherein said first glove and said second glove are composed of butyl rubber.

21. The water sampling device of claim 12, further comprising a stand secured to said four sidewalls of an exterior of said chamber adapted to support said chamber in an upright position.

22. The water sampling device of claim 21, wherein said stand comprises a first pair of parallel supports and a second pair of parallel supports, wherein said first pair of parallel supports are adjustably secured to said second pair of parallel supports by fasteners, such that said first pair of parallel supports are adapted to align with said second pair of parallel supports in a compact configuration.

23. The water sampling device of claim 22, wherein a cross section of each of said first pair of supports and said second pair of supports is L-shaped.

24. The water sampling device of claim 22, further comprising a locking mechanism, wherein said locking mechanism includes a first chain connecting a support from said first pair of supports to a support from said second pair of supports, and a second chain connecting a parallel support from said first pair of supports to a parallel support from said second pair of supports, such that said first pair of supports are secured at a desired angle relative to said second pair of supports.

* * * * *